United States Patent

Petrzilka et al.

Patent Number: 4,629,581
Date of Patent: Dec. 16, 1986

[54] CYCLOHEXANECARBONITRILES

[75] Inventors: Arthur Boller, Binningen; Martin Petrzilka, Kaiseraugst; Martin Schadt, Seltisberg, all of Switzerland

[73] Assignee: Hoffmann-La Roche Inc., Nutley, N.J.

[21] Appl. No.: 749,160

[22] Filed: Jun. 26, 1985

[30] Foreign Application Priority Data

Jun. 29, 1984 [CH] Switzerland .......................... 3152/84
Apr. 17, 1985 [CH] Switzerland .......................... 1638/85

[51] Int. Cl.[4] .................... C09K 3/34; C07C 121/46
[52] U.S. Cl. ........................ 252/299.63; 350/350 R; 558/426; 558/431
[58] Field of Search ............... 260/465 D, 464, 465 R; 252/299.63; 558/426, 431; 350/350 R

[56] References Cited

U.S. PATENT DOCUMENTS 4,510,069  4/1985  Eidenschink et al. ......... 252/299.61

FOREIGN PATENT DOCUMENTS 3231707  1/1984  Fed. Rep. of Germany .

OTHER PUBLICATIONS

R. Eidenschink et al., 4. Freiburger Arbeitstagung Flüssigkristalle, Apr. 3, 1984.

Primary Examiner—Dolph H. Torrence
Attorney, Agent, or Firm—Jon S. Saxe; Bernard S. Leon; Mark E. Waddell

[57] ABSTRACT

Compounds of the formula

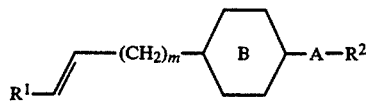

wherein $R^1$ is hydrogen or straight-chain alkyl; $R^2$ is —CN, —R, —COR, —COOR or when $R^2$ is positioned on an aromatic ring $R^2$ also can be —OR, —OOCR or —F; R is alkyl; A is a group with 1 to 4 six-membered rings, these rings being linked directly with one another and with ring B in each case via a single covalent bond or being linked at one or two positions also via —COO—, —OOC— or —CH$_2$CH$_2$—; the six-membered rings in A and ring B each are 1,4-phenylene or trans-1,4-cyclohexylene or one of these rings also is trans-2,5-disubstituted m-dioxane, 2,5-disubstituted pyrimidine or 3,6-disubstituted pyridazine, with the proviso that a maximum of two adjacent trans-1,4-cyclohexylene rings are linked directly via a single covalent bond; and m is the integer 2, or when ring B is trans-1,4-cyclohexylene or trans-2,5-disubstituted m-dioxane, m also can be the integer 0, their manufacture, liquid crystalline mixtures which contain these compounds as well as the use of these compounds for electro-optical purposes are described.

Additionally, compounds of the formula

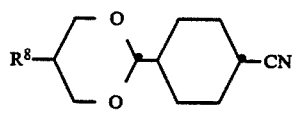

LXXVIII wherein $R^8$ is straight-chain $C_1$–$C_{12}$ alkyl, their manufacture, liquid crystalline mixtures which contain these compounds and their use for electro-optical purposes are described.

39 Claims, No Drawings

CYCLOHEXANECARBONITRILES

BACKGROUND OF THE INVENTION

1. Field of the Invention

The present invention is concerned with novel cyclohexanecarbonitriles, their manufacture, liquid crystalline mixtures which contain these compounds as well as their use for electro-optical purposes.

2. Description

Liquid crystals have recently gained considerable importance as dielectrics in indicating devices, since the optical properties of such substances can be influenced by an applied voltage. Electro-optical devices based on liquid crystals are well known to the person skilled in the art and can be based on various effects such as, for example, the dynamic scattering, the deformation of aligned phases (DAP type) the Schadt-Helfrich effect (twisted-nematic cell), the guest/host effect (guest/host cell) or a cholesteric-nematic phase transition (phase change effect).

The liquid crystals which are used must have a good stability towards heat, moisture, air, electromagnetic radiation, electrical fields and the like. Further, they should be colourless, should have short response times and low viscosity, should give a good contrast and should have a nematic or cholesteric mesophase in the entire temperature range in which the liquid crystal cell is to be operated. Since liquid crystals are usually used as mixtures, it is, moreover, important that the components have a good miscibility with one another and at the same time form a nematic or cholesteric mesophase. Other properties such as, for example, the electrical conductivity, the threshold potential, the multiplexibility and the dielectric anisotropy must fulfill different conditions depending on the type of cell which is used.

Liquid crystals with negative anisotropy of the dielectric constants ($\Delta\epsilon = \epsilon_\parallel - \epsilon_\perp$ less than 0, $\epsilon_\parallel$ signifying the dielectric constant along the longitudinal axis of the molecule and $\epsilon_\perp$ signifying the dielectric constant perpendicular thereto) can be used, for example, in liquid crystal cells of the light-scattering type, in DAP cells or in guest/host cells. Further, a two-frequency matrix addressing has been proposed (e.g. German Offenlegungsschriften Nos. 2856134 and 2907940, corresponding respectively to U.S. Pat. No. 4,417,785 and U.K. Pat. No. 2,020,075) in order to improve the multiplex ratio in the multiplex control of liquid crystal devices, especially of twisted-nematic cells and guest/host cells. In order to improve the dielectric anisotropy above the "cross-over frequency" (dielectric relaxation frequency at which $\epsilon_\parallel = \epsilon_\perp$), components with negative dielectric anisotropy can be added to the corresponding dielectrics (e.g. German Offenlegungsschrift 3221462, corresponding to U.S. Pat. No. 4,460,770).

Compounds with a large negative anisotropy of the dielectric constants are already known, examples of such compounds being pyridazines, pyridazine oxides and compounds containing a 2,3-dicyano-1,4-phenylene group. However, these compounds have various disadvantages such as e.g. poor solubility in mixtures, high viscosities, high melting points, strong smectic tendencies, chemical instability, high electrical conductivity or large clearing point depressions in mixtures and are therefore usable only to a very limited extent.

SUMMARY OF THE INVENTION

It has now been found that the compounds of the formula

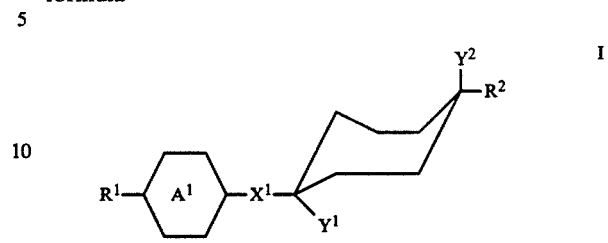

wherein $X^1$ represents a single covalent bond, $-CH_2CH_2-$, $-COO-$, $-OOC-$ or 1,4-phenylene; one of the symbols $Y^1$ and $Y^2$ denotes hydrogen and the other denotes cyano; $R^2$ signifies trans-1-alkenyl, cis-2-alkenyl, trans-3-alkenyl, 4-alkenyl or alkyl; $R^1$ stands for the group $R^{11}-A^4-A^5-$ and $A^4$ and $A^5$ independently of each other represent a single covalent bond, 1,4-phenylene or trans-1,4-cyclohexylene; $R^{11}$ signifies trans-1-alkenyl, cis-2-alkenyl, trans-3-alkenyl, 4-alkenyl, trans-2-alkenyloxy, 3-alkenyloxy or, when $R^2$ stands for an alkenyl group, $R^{11}$ also can be alkyl or alkoxy; ring $A^1$ represents 1,4-phenylene or a group of the formula

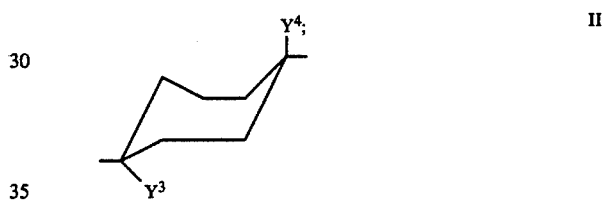

and $Y^3$ and $Y^4$ denote hydrogen or, when $X^1$ represents $-CH_2CH_2-$, $-COO-$ or $-OOC-$, one of the symbols $Y^3$ and $Y^4$ also can denote cyano, have a relatively large negative anisotropy of the dielectric constants, good miscibility with other liquid crystal components and low viscosity. They are colourless and have a good chemical stability.

The invention also concerns the manufacture of the compounds of formula I, liquid crystalline mixtures which contain these compounds as well as their use for electro-optical purposes.

DETAILED DESCRIPTION OF THE INVENTION

The present invention is concerned with novel cyclohexanecarbonitriles of the formula:

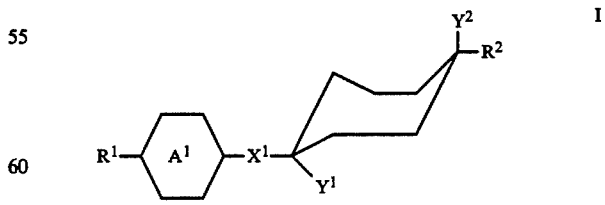

wherein $X^1$ is a single covalent bond, $-CH_2CH_2-$, $-COO-$, $-OOC-$ or 1,4-phenylene; one of $Y^1$ and $Y^2$ denotes hydrogen and the other denotes cyano; $R^2$ is trans-1-alkenyl, cis-2-alkenyl, trans-3-alkenyl, 4-alkenyl or alkyl; $R^1$ is $R^{11}-A^4-A^5-$; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy; ring $A^1$ is 1,4-phenylene or a group of the formula

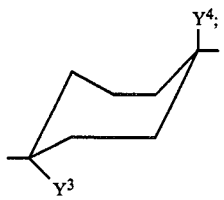
II and $Y^3$ and $Y^4$ each are hydrogen or, when $X^1$ is —CH$_2$CH$_2$—, —COO— or —OOC—, one of $Y^3$ and $Y^4$ also can be cyano.

The compounds of formula I have a relatively large negative anisotropy of the dielectric constants, good miscibility with other liquid crystal components and low viscosity. They are colourless and have a good chemical stability. The compounds of formula I in which $R^1$ and/or $R^2$ contain a trans-1-alkenyl, trans-3-alkenyl or trans-2-alkenyloxy group have an expecially favourable mesophase range, while the compounds of formula I in which $R^1$ and/or $R^2$ contain a cis-2-alkenyl, 4-alkenyl or 3-alkenyloxy group have primarily a favourable ratio of the elastic constants $k_{33}$ (bend) and $K_{11}$ (splay) and give comparatively low threshold potentials. The compounds in accordance with the invention are accordingly especially suitable as components of liquid crystal mixtures with negative dielectric anisotropy and as components of liquid crystal mixtures which are used in the two-frequency matrix addressing. The compounds of formula I in which $A^4$ and $A^5$ signify single covalent bonds, i.e. $R^1$ stands for $R^{11}$, are suitable primarily as basic components having low viscosity, while the remaining compounds of formula I are useful mainly as additives for increasing the clearing point. The compounds in accordance with the invention can, however, also be used in mixtures with positive dielectric anisotropy, for example in order to adapt the threshold potential to the electro-optical cell which is used.

In the scope of the present invention (unless indicated otherwise) the term "alkyl" denotes straight chain alkyl groups of 1 to 12 carbon atoms (e.g., methyl, ethyl, propyl, butyl, pentyl, hexyl, heptyl, octyl, nonyl, decyl, undecyl and dodecyl). The term "trans-1-alkenyl" embraces 1E-alkenyl residues such as vinyl, 1E-propenyl, 1E-butenyl, 1E-pentenyl, 1E-hexenyl, 1E-heptenyl, 1E-octenyl, 1E-nonenyl, 1E-decenyl, 1E-undecenyl and 1E-dodecenyl. The term "cis-2-alkenyl" embraces 2Z-alkenyl residues such as 2-propenyl, 2Z-butenyl, 2Z-pentenyl, 2Z-hexenyl, 2Z-heptenyl, 2Z-octenyl, 2Z-nonenyl, 2Z-decenyl, 2Z-undecenyl and 2Z-dodecenyl. The term "trans-3-alkenyl" embraces 3E-alkenyl residues such as 3-butenyl, 3E-pentenyl, 3E-hexenyl, 3E-heptenyl, 3E-octenyl, 3E-nonenyl, 3E-decenyl, 3E-undecenyl and 3E-dodecenyl. The term "4-alkenyl" embraces residues such as 4-pentenyl and the E- and/or Z-form of 4-hexenyl, 4-heptenyl, 4-octenyl, 4-nonenyl, 4-decenyl, 4-undecenyl and 4-dodecenyl. The term "alkoxy" embraces preferably straight-chain alkoxy such as methoxy, ethoxy, propyloxy, butyloxy, pentyloxy, hexyloxy, heptyloxy, octyloxy, nonyloxy, decyloxy, undecyloxy and dodecyloxy. The term "trans-2-alkenyloxy" embraces 2E-alkenyloxy residues such as 2-propenyloxy, 2E-butenyloxy, 2E-pentenyloxy, 2E-hexenyloxy, 2E-heptenyloxy, 2E-octenyloxy, 2E-nonenyloxy, 2E-decenyloxy, 2E-undecenyloxy and 2E-dodecenyloxy. The term "3-alkenyloxy" embraces residues such as 3-butenyloxy and the E- and/or Z-form of 3-pentenyloxy, 3-hexenyloxy, 3-heptenyloxy, 3-octenyloxy, 3-nonenyloxy, 3-decenyloxy, 3-undecenyloxy and 3-dodecenyloxy.

In the scope of the present invention the term "halogen" signifies chlorine, bromine or iodine and the term "alkali metal" signifies lithium, sodium or potassium. The term "aryl" signifies phenyl, tolyl and the like.

Formula I above embraces the following formulae:

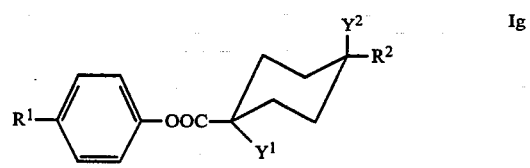
Ig

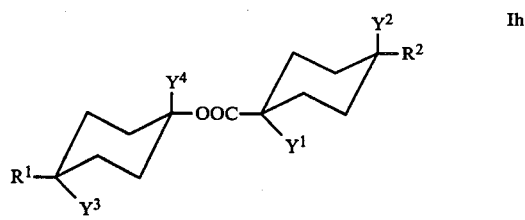
Ih

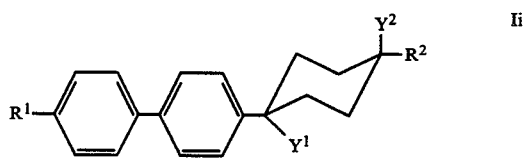
Ii

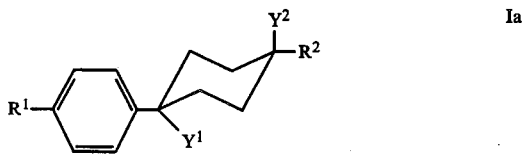
Ia

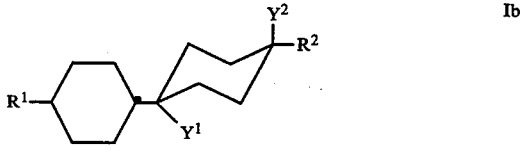
Ib

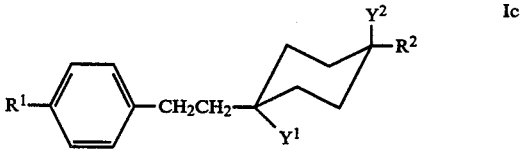
Ic

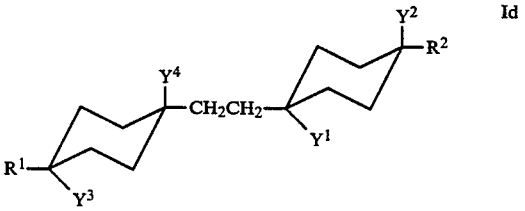
Id

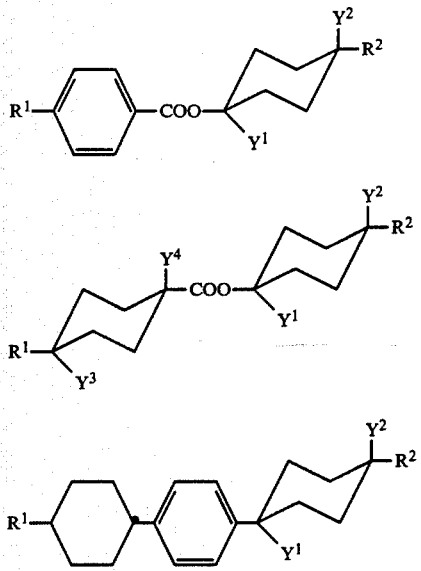

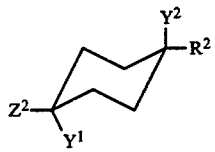

wherein one of $Y^1$ and $Y^2$ is hydrogen and the other is cyano; $Y^3$ and $Y^4$ denote hydrogen or one of $Y^3$ and $Y^4$ also can denote cyano; and $R^1$ and $R^2$ have the above significances.

Preferred compounds of formula I and of formulae Ia–Ij are those in which $A^5$ represents a single covalent bond. Those compounds in which $A^4$ and $A^5$ represent single covalent bonds, i.e. $R^1$ stands for $R^{11}$, are especially preferred.

$R^{11}$ and $R^2$ preferably stand for straight-chain residues with a maximum of 12 carbon atoms, especially for straight-chain trans-1-alkenyl with 2 to 12 carbon atoms, straight-chain cis-2-alkenyl with 3 to 12 carbon atoms, straight-chain trans-3-alkenyl with 4 to 12 carbon atoms, straight-chain 4-alkenyl with 5 to 12 carbon atoms or one of the residues $R^{11}$ and $R^2$ also stands for straight-chain alkyl with 1 to 12 carbon atoms. Residues $R^{11}$ and $R^2$ with a maximum of 7 carbon atoms are especially preferred.

Preferably, $R^{11}$ and $R^2$ independently of each other signify trans-1-alkenyl, trans-3-alkenyl or 4-alkenyl or one of the residues $R^{11}$ and $R^2$, preferably $R^{11}$, also signifies alkyl. The compounds of formula I or of formulae Ia–Ij in which one of the residues $R^{11}$ and $R^2$ signifies trans-3-alkenyl and the other signifies trans-1-alkenyl, trans-3-alkenyl, 4-alkenyl or alkyl are especially preferred.

In the compounds of formula I in which ring $A^1$ represents 1,4-phenylene, i.e. in the compounds of formulae Ia, Ic, Ie, Ig and Ii, $R^1$ preferably signifies trans-3-alkenyl, 4-alkenyl or alkyl.

4-Alkenyl residues which may be present in $R^1$ and-/or $R^2$ and a 3-alkenyloxy residue which may be present in $R^1$ preferably have the Z-form.

3-Butenyl, 4-pentenyl, 3E-pentenyl and 1E-pentenyl are especially preferred alkenyl residues.

Preferred compounds of formula Id are those in which $Y^3$ and $Y^4$ signify hydrogen, as well as those in which $Y^4$ and at the same time $Y^2$ signify cyano. Of the remaining compounds of formula I there are generally preferred those in which $Y^2$ signifies cyano and substituents $Y^3$ and $Y^4$ which may be present signify hydrogen.

Furthermore, there are generally preferred those compounds of formula I in which ring $A^1$ represents trans-1,4-cyclohexylene, i.e. the compounds of formulae Ib and Ij and the compounds of formulae Id, If and Ih in which $Y^3$ and $Y^4$ denote hydrogen.

The compounds of formula I can be manufactured in accordance with the invention by the following procedure:

(a) for the manufacture of the compounds of formula I in which $X^1$ represents —COO— or —OOC—, esterifying a compound of the formula

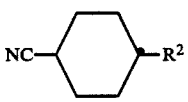

with a compound of the formula

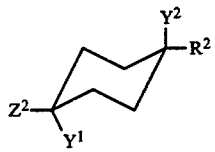

wherein one of the groups $Z^1$ and $Z^2$ signifies —COOH or —COCl and the other signifies —OH; ring $A^1$ represents 1,4-phenylene or a group of formula II above; $Y^3$ and $Y^4$ in formula II denote hydrogen or one of these symbols also denotes cyano; and $R^1$, $R^2$, $Y^1$ and $Y^2$ have the above significances, or (b) for the manufacture of the compounds of formula I in which $X^1$ represents a single covalent bond, —CH$_2$CH$_2$— or 1,4-phenylene, $Y^2$ denotes cyano and $R^2$ signifies cis-2-alkenyl, trans-3-alkenyl, 4-alkenyl or alkyl, reacting a compound of the formula

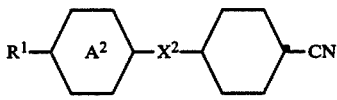

firstly with base and then with a compound of the formula $$Z^3\text{-}R^5 \qquad \text{VI}$$

wherein $X^2$ represents a single covalent bond, —CH$_2$CH$_2$— or 1,4-phenylene; ring $A^2$ denotes 1,4-phenylene or a group of formula II; $Y^3$ and $Y^4$ in formula II signify hydrogen or, insofar as $X^2$ represents —CH$_2$CH$_2$—, one of the symbols $Y^3$ and $Y^4$ also denotes cyano; $Z^3$ denotes halogen; $R^5$ signifies cis-2-alkenyl, trans-3-alkenyl, 4-alkenyl or alkyl; and $R^1$ has the above significance, or (c) for the manufacture of the compounds of formula I in which $X^1$ represents a single covalent bond or —CH$_2$CH$_2$—, ring $A^1$ signifies trans-1,4-cyclohexylene and $Y^1$ denotes cyano, reacting a compound of the formula

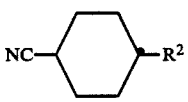

firstly with base and then with a compound of the formula

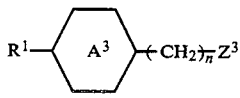  VIII wherein n stands for the number 0 and ring $A^3$ stands for cis-1,4-cyclohexylene or n stands for the number 2 and ring $A^3$ stands for trans-1,4-cyclohexylene; $Z^3$ denotes halogen; and $R^1$ and $R^2$ have the above significances, or (d) for the manufacture of the compounds of formula I in which $X^1$ represents a single covalent bond, —$CH_2CH_2$— or 1,4-phenylene and $Y^1$ denotes cyano, reacting a compound of the formula

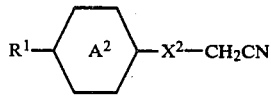  IX firstly with base and then with a compound of the general formula

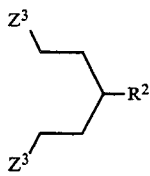  X wherein $X^2$ represents a single covalent bond, —$CH_2$-$CH_2$— or 1,4-phenylene; ring $A^2$ denotes 1,4-phenylene or a group of formula II; $Y^3$ and $Y^4$ in formula II signify hydrogen or, insofar as $X^2$ represents —$CH_2CH_2$—, one of the symbols $Y^3$ and $Y^4$ also denotes cyano; $Z^3$ denotes halogen; and $R^1$ and $R^2$ have the above significances. or (e) for the manufacture of the compounds of formula I in which $X^1$ represents a single covalent bond, —$CH_2CH_2$— or 1,4-phenylene, $Y^2$ denotes cyano and $R^2$ signifies trans-1-alkenyl, reacting a compound of the formula

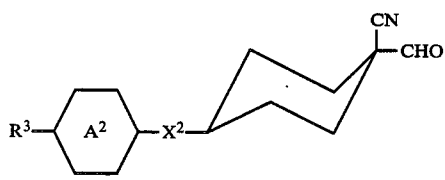  XI wherein $X^2$ represents a single covalent bond, —$CH_2$-$CH_2$— or 1,4-phenylene; ring $A^2$ denotes 1,4-phenylene or a group of formula II; $Y^3$ and $Y^4$ in formula II signify hydrogen or, insofar as $X^2$ represents —$CH_2CH_2$—, one of the symbols $Y^3$ and $Y^4$ also denotes cyano; and $R^3$ has the significances given for $R^1$ in formula I. in the presence of a base with an alkyl-triarylphosphonium halide, or (f) for the manufacture of the compounds of formula I in which $X^1$ represents a single covalent bond, —$CH_2CH_2$— or 1,4-phenylene, adding HCN to a compound of the formula

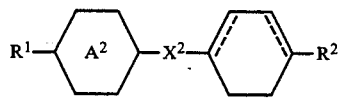  XII wherein $X^2$ represents a single covalent bond, —$CH_2C$-$H_2$— or 1,4-phenylene; ring $A^2$ denotes 1,4-phenylene or a group of formula II; $Y^3$ and $Y^4$ in formula II signify hydrogen or, insofar as $X^2$ represents —$CH_2CH_2$—, one of the symbols $Y^3$ and $Y^4$ also denotes cyano, one of the dotted lines denotes an additional bond; and $R^1$ and $R^2$ have the above significances, or (g) for the manufacture of the compounds of formula I in which $X^1$ represents a single covalent bond, —$CH_2CH_2$— or 1,4-phenylene and $R^1$ signifies trans-2-alkenyloxy, 3-alkenyloxy or alkoxy, etherifying a compound of the formula

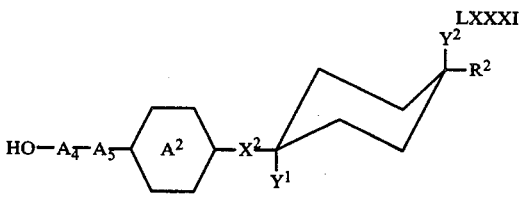  LXXXI wherein $X^2$ represents a single covalent bond, —$CH_2C$-$H_2$— or 1,4-phenylene; ring $A^2$ denotes 1,4-phenylene or a group of formula II; $Y^3$ and $Y^4$ in formula II signify hydrogen or, insofar as $X^2$ represents —$CH_2CH_2$—, one of the symbols $Y^3$ and $Y^4$ also denotes cyano; and $A^4$, $A^5$, $R^2$, $Y^1$ and $Y^2$ have the significances given in formula I, with a trans-2-alkenyl halide, a 3-alkenyl halide or an alkyl halide.

The esterification of a compound of formula III with a compound of formula IV (process variant a) can be carried out in a manner known per se. The esterification of the acid chlorides (which are obtainable from the carboxylic acids e.g. by heating with thionyl chloride) can be carried out, for example, in diethyl ether, tetrahydrofuran, dimethylformamide, benzene, toluene, carbon tetrachloride, pyridine and the like. The esterification of the carboxylic acids is preferably carried out in the presence of 4-(dimethylamino)pyridine and dicyclohexylcarbodiimide or in the presence of oxalyl chloride and dimethylformamide. The temperature and pressure at which these esterification reactions are carried out are not critical. In general, atmospheric pressure and a temperature between about −30° C. and the boiling temperature of the reaction mixture are used.

The reaction of a nitrile of formula V, VII or IX with base and subsequently with a halide of formula VI, VIII or X (process variants b-d) can also be carried out in a manner known per se. The preferred halogen $Z^3$ is bromine. Suitable bases are, for example, sodium hydride, sodium amide, lithium diisopropylamide, potassium t-butylate and the like. Preferred bases are the alkali metal dialkylamides in which the term "alkyl" preferably signifies straight-chain or branched residues with 1 to 5 carbon atoms. Lithium diisopropylamide is the especially preferred base. The reaction is conveniently carried out in an inert organic solvent, for example an ether, an aromatic hydrocarbon, an amide or a sulphoxide, such as tetrahydrofuran, dioxan, diethyl ether, toluene, dimethylformamide or dimethyl sulphoxide. The temperature and pressure are not critical; in general, however, process variants b and c are carried out at atmospheric pressure and a temperature of about −80° C. to room temperature and process variant d is carried out at atmospheric pressure and a temperature of about 0°–150° C.

The reaction of a compound of formula XI with an alkyl-triarylphosphonium halide, preferably an alkyl-triphenylphosphonium chloride or alkyl-triphenylphosphonium bromide (process variant e), can also be carried out in a manner known per se. Suitable bases are the bases named above under process variants b-d. Preferred bases are, however, the alkali metal carbonates and especially the alkali metal alcoholates with 1 to 5 carbon atoms. Potassium carbonate, sodium methylate and potassium t-butylate are examples of preferred bases. The reaction is conveniently carried out in an inert organic solvent, for example an ether such as diethyl ether, tetrahydrofuran or dioxan. The temperature and pressure are not critical; in general, however, the reaction is carried out at atmospheric pressure and a temperature from room temperature to the reflux temperature.

The addition of HCN to a compound of formula XII (process variant f) can also be carried out in a manner known per se. The reaction is conveniently carried out in an inert organic solvent, for example a nitrile, amide or chlorinated hydrocarbon such as acetonitrile, dimethylformamide, methylene chloride or chloroform. The temperature and pressure are not critical; in general, however, the reaction is carried out at a temperature of about −10° C. to 150° C. and a pressure of about 1–10 bar. If desired, the reaction can also be carried out in the presence of a catalyst such as palladium-bis-[2,3,-O-isopropylidene-2,3-dihydroxy-1,4-bis(diphenylphosphino)butane] and the like.

The etherification of a compound of formula LXXXI (process variant g) can also be carried out in a manner known per se. The reaction is conveniently carried out in an inert organic solvent in the presence of a base such as sodium hydride, sodium, sodium carbonate, potassium carbonate and the like. Preferred halides are the bromides and especially the iodides. The reaction is preferably carried out at atmospheric pressure and a temperature from room temperature to the reflux temperature.

The compounds of formulae III-V, VII-X and LXXXI in which $R^1$ or $R^2$ has an alkyl or alkoxy group and the compounds of formula VI are known compounds or analogues of known compounds.

The remaining starting materials, i.e. the compounds of formulae III-V, VII-X and LXXXI in which $R^1$ or $R^2$ has an alkenyl or alkenyloxy group and the compounds of formulae XI and XII are novel. The preparation of these starting materials is illustrated on the basis of the following Reaction Schemes 1-12 in which R signifies alkyl, $R^4$ signifies hydrogen or alkyl and THP signifies the tetrahydropyranyl group, $R^5$ denotes cis-2-alkenyl, trans-3-alkenyl, 4-alkenyl or alkyl and $R^1$, $R^2$, $R^3$, $X^2$ and ring $A^2$ have the above significances.

Scheme 1

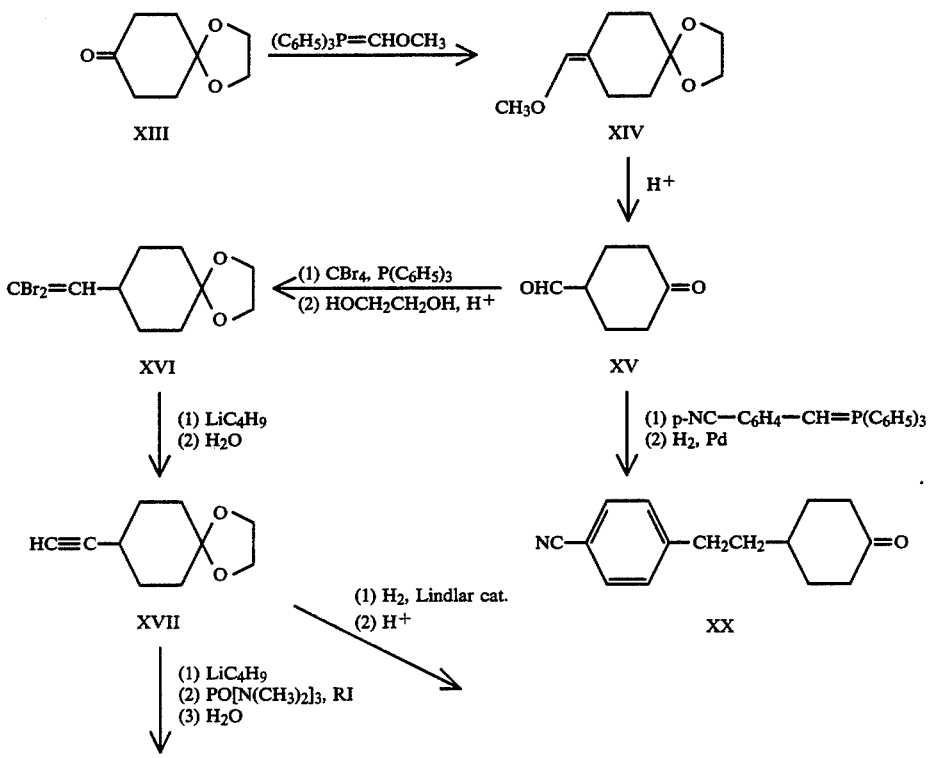

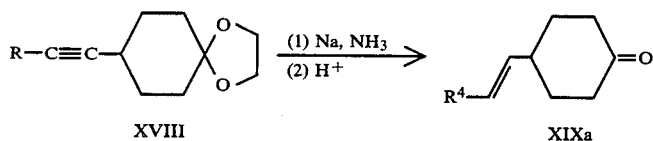
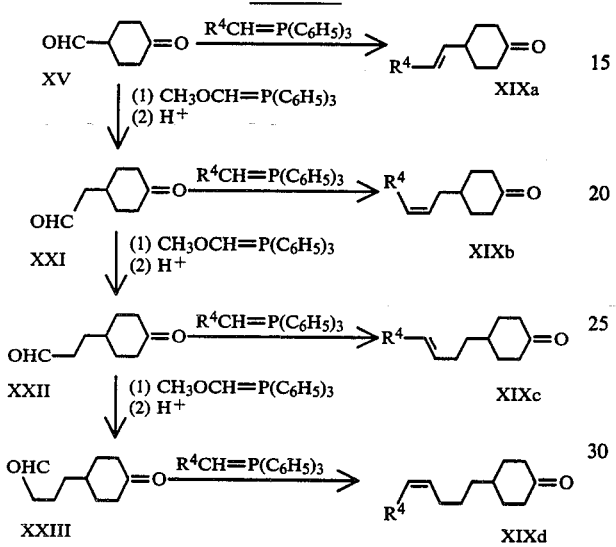
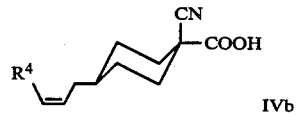
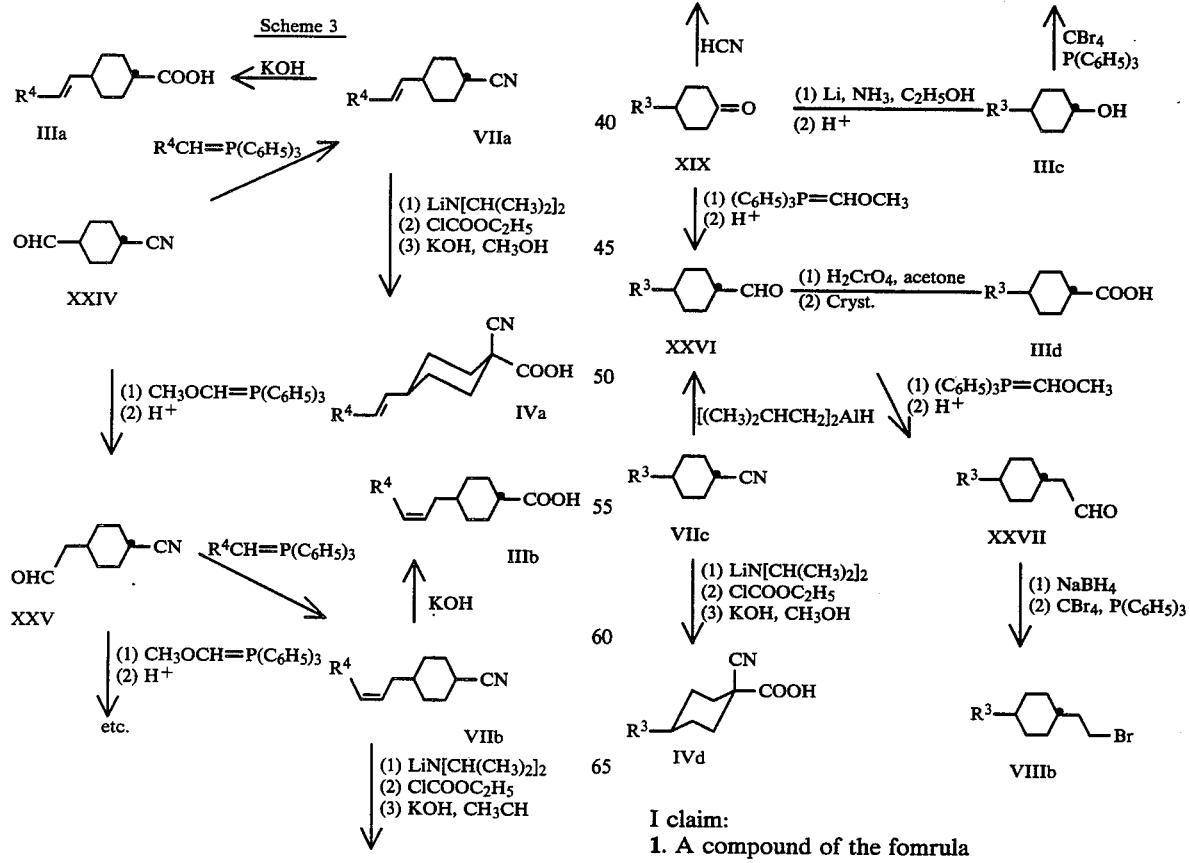
I claim:
1. A compound of the formula

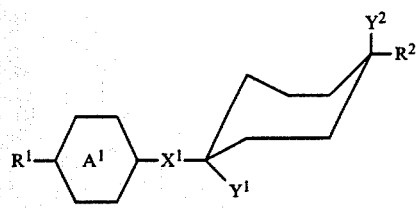
I wherein $X^1$ is a single covalent bond, —$CH_2CH_2$—, —COO—, —OOC— or 1,4-phenylene; one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy; ring $A^1$ is 1,4-phenylene or a group of the formula

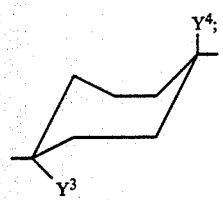
II and $Y^3$ and $Y^4$ are hydrogen or, when $X^1$ is —$CH_2CH_2$—, —COO— or —OOC—, one of $Y^3$ and $Y^4$ also can be cyano.

2. The compounds of claim 1, wherein $R^1$ and $R^2$ independently of each other are trans-1-alkenyl, cis-2-alkenyl, trans-3-alkenyl or 4-alkenyl or one of $R^1$ and $R^2$ also can be alkyl; and $Y^3$ and $Y^4$ are hydrogen or when $X^1$ is —COO— or —OOC—, one of $Y^3$ and $Y^4$ also can be cyano.

3. The compound of claim 1, wherein $X^1$ is —$CH_2CH_2$—, $R^1$ and $R^2$ independently of each other are trans-1-alkenyl, cis-2-alkenyl, trans-3-alkenyl or 4-alkenyl, or one of $R^1$ and $R^2$ also can be alkyl; ring $A^1$ is a group of formula II, and one of $Y^3$ and $Y^4$ is hydrogen and the other is cyano.

4. The compound of claim 2, wherein $R^1$ and $R^2$ each have a maximum of 12 carbon atoms.

5. The compound of claim 4, wherein $R^1$ and $R^2$ each have a maximum of 7 carbon atoms.

6. The compound of claim 3, wherein $R^1$ and $R^2$ each have a maximum of 12 carbon atoms.

7. The compound of claim 6 wherein $R^1$ and $R^2$ each have a maximum of 7 carbon atoms.

8. The compound of claim 2, wherein $R^1$ and $R^2$ independently of each other are trans-1-alkenyl, trans-3-alkenyl or 4-alkenyl or one of $R^1$ and $R^2$ also can be alkyl.

9. The compound of claim 8 wherein $R^1$ is alkyl.

10. The compound of claim 3, wherein $R^1$ and $R^2$ independently of each other are trans-1-alkenyl, trans-3-alkenyl or 4-alkenyl or one of $R^1$ and $R^2$ also can be alkyl.

11. The compound of claim 10 wherein $R^1$ is alkyl.

12. The compound of claim 8, wherein one of $R^1$ and $R^2$ is trans-3-alkenyl and the other is trans-1-alkenyl, trans-3-alkenyl, 4-alkenyl or alkyl.

13. The compound of claim 10, wherein one of $R^1$ and $R^2$ is trans-3-alkenyl and the other is trans-1-alkenyl, trans-3-alkenyl, 4-alkenyl or alkyl.

14. The compound of claim 1, wherein each of $Y^1$ and $Y^3$ is hydrogen and $Y^2$ is cyano.

15. The compound of claim 2, wherein each of $Y^1$ and $Y^3$ is hydrogen and $Y^2$ is cyano.

16. The compound of claim 3, wherein each of $Y^1$ and $Y^3$ is hydrogen and $Y^2$ is cyano.

17. The compound of claim 1 wherein $A^5$ is a single covalent bond.

18. The compond of claim 17 wherein $A^4$ and $A^5$ are single covalent bonds.

19. The compound of claim 1 having the formula

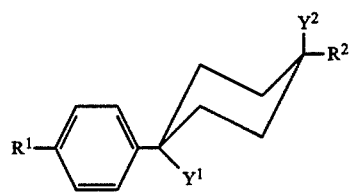
Ia wherein one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

20. The compound of claim 19 wherein $R^1$ is trans-3-alkenyl, 4-alkenyl or alkyl.

21. The compound of claim 1 having the formula

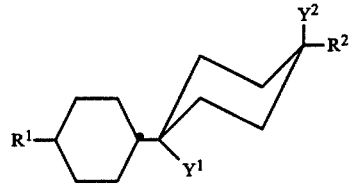
Ib wherein one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

22. The compound of claim 1 having the formula

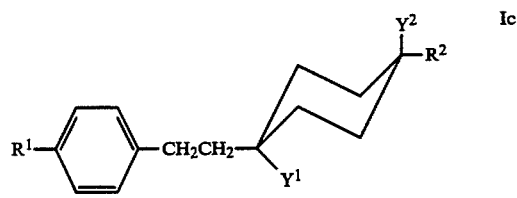
Ic wherein one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

23. The compound of claim 22 wherein $R^1$ is trans-3-alkenyl, 4-alkenyl or alkyl.

24. The compound of claim 1 having the formula

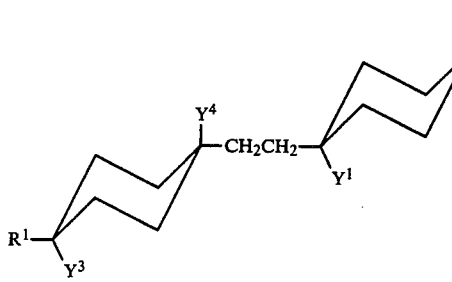

wherein one of $Y^1$ and $Y^2$ is hydrogen and the other is cyano; $Y^3$ and $Y^4$ are hydrogen or one of $Y^3$ and $Y^4$ is cyano and the other is hydrogen; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

25. The compound of claim 24 wherein $Y^3$ and $Y^4$ are hydrogen.

26. The compound of claim 24 wherein $Y^4$ and $Y^2$ are cyano.

27. The compound of claim 1 having the formula

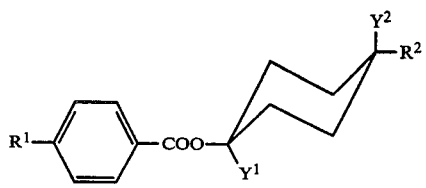

wherein one of $Y^1$ and $Y^2$ are hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

28. The compound of 27 wherein $R^1$ is trans-3-alkenyl, 4-alkenyl or alkyl.

29. The compound of claim 1 having the formula

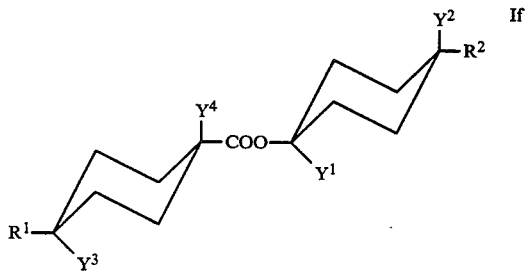

wherein one of $Y^1$ and $Y^2$ is hydrogen and the other is cyano; $Y^3$ and $Y^4$ are hydrogen or one of $Y^3$ and $Y^4$ is cyano and the other is hydrogen; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

30. The compound of claim 29 wherein $Y^3$ and $Y^4$ are hydrogen.

31. The compound of claim 1 having the formula

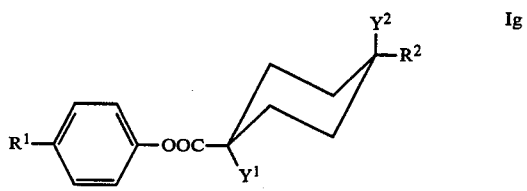

wheein one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

32. The compound of claim 31 wherein $R^1$ is trans-2-alkenyl, 4-alkenyl or alkyl.

33. The compound of claim 1 having the formula

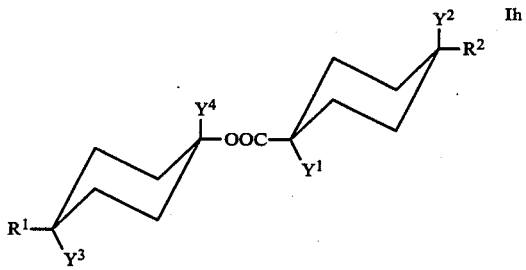

wherein one of $Y^1$ and $Y^2$ is hydrogen and the other is cyano; $Y^3$ and $Y^4$ are hydrogen or one of $Y^3$ and $Y^4$ is cyano and the other is hydrogen; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

34. The compound of claim 33 wherein $Y^3$ and $Y^4$ are hydrogen.

35. The compound of claim 1 having the formula

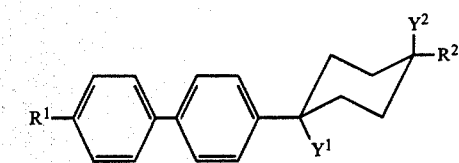
Ii wherein one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

36. The compound of claim 35 wherein $R^1$ is trans-3-alkenyl, 4-alkenyl or alkyl.

37. The compound of claim 1 having the formula

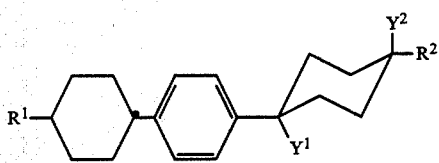
Ij wherein one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy.

38. A liquid crystalline mixture comprising at least two components at least one of which is a compound of the formula

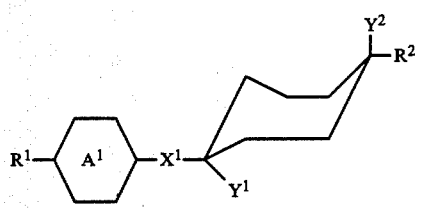
I wherein $X^1$ is a single covalent bond, —CH$_2$CH$_2$—, —COO—, —OOC— or 1,4-phenylene; one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy; ring $A^1$ is 1,4-phenylene or a group of the formula

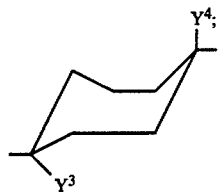
II

39. An electro-optical cell comprising:
(a) two plate means;
(b) a liquid crystalline means disposed between the two plate means and including a compound of the formula

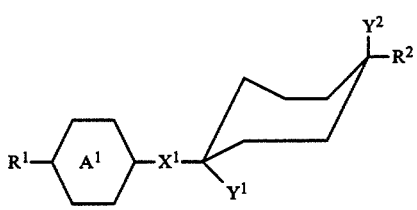
I wherein $X^1$ is a single covalent bond, —CH$_2$CH$_2$—, —COO—, —OOC— or 1,4-phenylene; one of $Y^1$ and $Y^2$ is hydrogen and the other is cyano; $R^2$ is trans-1-alkenyl, cis-2-alkenyl, trans-3-alkenyl, 4-alkenyl or alkyl; $R^1$ is $R^{11}$—$A^4$—$A^5$—; $A^4$ and $A^5$ independently of each other are a single covalent bond, 1,4-phenylene or trans-1,4-cyclohexylene; $R^{11}$ is trans-1-alkenyl, cis-2-alkenyl, trans-3-alkenyl, 4-alkenyl, trans-2-alkenyloxy, 3-alkenyloxy or, when $R^2$ is alkenyl, $R^{11}$ also can be alkyl or alkoxy; ring $A^1$ is 1,4-phenylene or a group of the formula

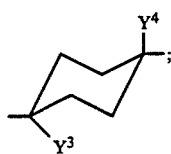
II and $Y^3$ and $Y^4$ are hydrogen or, when $X^1$ is —CH$_2$CH$_2$—, —COO— or —OOC—, one of $Y^3$ and $Y^4$ also can be cyano; and
(c) means for applying an electric potential to said plate means.

* * * * *